United States Patent [19]

Lakshmanan et al.

[11] Patent Number: 5,084,389
[45] Date of Patent: Jan. 28, 1992

[54] BIOADSORPTION COMPOSITION AND PROCESS FOR PRODUCTION THEREOF

[75] Inventors: V. I. Lakshmanan, Mississauga; R. G. L. McCready, Kanata, both of Canada

[73] Assignee: Her Majesty in Right of Canada as represented by the Minister of Energy, Mines and Resources Canada, Ontario, Canada

[21] Appl. No.: 387,930

[22] Filed: Aug. 1, 1989

[51] Int. Cl.[5] .................. C12N 11/14; B01J 37/36; B01J 30/34
[52] U.S. Cl. .................. 435/176; 423/DIG. 17; 423/6; 423/182; 435/182; 502/7; 502/401; 502/403; 502/405; 210/616; 210/617
[58] Field of Search .............. 502/7, 403, 401, 405; 423/DIG. 17; 435/176, 182

[56] References Cited

U.S. PATENT DOCUMENTS

| | | | |
|---|---|---|---|
| 3,912,593 | 10/1975 | Barker et al. | 502/7 |
| 4,021,368 | 5/1977 | Nemec et al. | 423/6 |
| 4,320,093 | 3/1982 | Volesky et al. | 502/405 |
| 4,461,832 | 7/1984 | Tschang et al. | 435/176 |
| 4,797,358 | 1/1989 | Kotai et al. | 435/182 |

FOREIGN PATENT DOCUMENTS

| | | |
|---|---|---|
| 0094979 | 5/1982 | European Pat. Off. |
| 2912827 | 10/1980 | Fed. Rep. of Germany ...... 435/182 |

*Primary Examiner*—Paul E. Konopka
*Attorney, Agent, or Firm*—Lowe, Price, LeBlanc & Becker

[57] ABSTRACT

A novel bioadsorption composition suitable for removing heavy metal from waster water effluent, the composition comprising a biomass encapsulated sol-gel matrix. A process for preparing the biomass encapsulated sol-gel matrix is also provided. The bioadsorption composition may be suitably used to remove a substantial amount heavy metal (such as uranium) from a waste water effluent, particularly a dilute aqueous stream comprising a waste water effluent (such as mine water). Heavy metal may then be recovered from the bioadsorption composition, thereby rendering the latter as reusable.

19 Claims, No Drawings

BIOADSORPTION COMPOSITION AND PROCESS FOR PRODUCTION THEREOF

FIELD OF THE INVENTION

In one of its aspects, the present invention relates to a novel bioadsorption composition. In another of its aspects, the present invention relates to a process for producing novel bioadsorption compositions In yet another of its aspects, the present invention relates to a process whereby a bioadsorption composition is utilized to remove heavy metal from a waste water effluent.

BACKGROUND OF THE INVENTION

It is known that certain microorganisms can selectively accumulate heavy metal ions from aqueous systems such as waste water effluents from metallurgical and mining operations. Thus, it is possible that these microorganisms may play an important role in the regulation of environmental pollution and in the recovery of useful metals from nature. The known processes which utilize these microorganisms are currently under intense scrutiny and investigation, but are, in general, not well understood.

Living cells have been known to concentrate cations from their aqueous environment. Further, microbial biomass has been demonstrated to exhibit a selective retention of heavy metals and transition metal elements as discussed above. It is believed that the ion exchange properties of the natural polysaccharides present in the walls of living cells may be at least partially responsible. Indications are that microbial cell walls possess the ability to bind with certain cations and inhibit them from becoming pollutants. An example of this type of process is taught by European Patent Application 0,094,979 (Skagerson) wherein there is disclosed a process for the retention of a high concentration of chromium in live yeast cells by intracellular adsorption. Another example of this type of process is taught by U.S. Pat. No. 4,320,093 (Volesky) wherein there is disclosed a technique for the removal of uranium and thorium cations from solution using a fungal microorganism of the genus Rhizopus.

It has been found, however, that the microorganisms used in these and similar metal recovery processes are destroyed by repeated contact with particulates and toxins from the waste water effluent to be treated. In particular, it has been found that fibrous biomass such as *Penicillin sp* disintegrates on repeated usage. The ability of these microorganisms to absorb and extract metals is reduced as the structure and integrity of the microorganisms are destroyed and, accordingly, they are not suitable for large scale operations where the microorganisms will be subjected to repeated contact with the dilute aqueous stream which typically comprise waste water effluent.

To enhance the commercial application of the microbial extraction of metals, attempts have been made to immobilize or stabilize the microorganism prior to exposure to the waste water effluent.

U.S. Pat. No. 4,021,368 (Nemec et al) discloses a process for retention of metal ions, such as uranium, from solution. More specifically, the process comprises using biomass of mycelia of fibrous fungi, stiffened by adding to the biomass polymerizible components, effecting polymerization thereof, and mechanically granulating the product.

A general review of procedures available for the immobilization of microorganisms is found in "Immobilized Cells and Organelles" by Mattiasson, B.; Vol. 1; CRC Press, Inc. More specifically, this reference addresses entrapment of cells with synthetic polymers such as polyacrylamide and polyurethane, and with natural polymers such as agarose and cellulose. It has been found, however, that polyacrylamide is a relatively difficult material with which to work. Complex equipment is required for reactions involving polyacrylamide and generally, the material is costly for immobilization techniques.

SUMMARY OF THE INVENTION

It is an object of the present invention to provide a novel bioadsorption composition which obviates or mitigates, at least in part, one or more of the above-mentioned disadvantages associated with the prior art.

It is another object of the present invention to provide a process for the production of a bioadsorption composition.

It is yet another object of the present invention to provide a process for removing heavy metal from a waste water effluent.

Accordingly, in one of its aspects, the present invention provides a bioadsorption composition suitable for removing heavy metal from waste water effluents, the bioadsorption composition comprising a biomass encapsulated sol-gel matrix.

In another of its aspects, the present invention provides a process for producing a biomass encapsulated sol-gel matrix suitable for use in a bioadsorption composition, the process comprising the steps of:
(i) reacting a biomass, a matrix compound and a metal compound to obtain thereby a sol;
(ii) hydrolyzing the sol to form thereby a dispersion of the sol-gel matrix; and
(iii) filtering and drying the filter residue of said dispersion to obtain thereby the sol-gel matrix;
wherein the matrix compound comprises at least one member selected from the group comprising silicates, aluminates and compounds comprising magnesium ion.

In yet another of its aspects, the present invention provides a process for removing heavy metals from a waste water effluent, said process comprising the steps of:
(i) providing a bioadsorption composition comprising a biomass encapsulated sol-gel matrix;
(ii) contacting with and passing through said bioadsorption composition a heavy metal bearing waste water effluent;
wherein a substantial amount of heavy metal from said waste water effluent is adsorbed by said bioadsorption composition.

DETAILED DESCRIPTION OF THE PREFERRED EMBODIMENTS

Thus, the bioadsorption composition of the present invention comprises biomass which is encapsulated within a sol-gel matrix.

The use of sol-gel processes in the field of nuclear fuel production is known. However, to the knowledge of the inventors, the application of these processes to the immobilization of biomass is novel and results in bioadsorption compositions which exhibit surprising and advantageous properties.

An important feature of most sol-gel processes is the preparation of small-sized (e.g. 15 to 200 Å) crystallites of the solid starting material which are thereafter linked up into an open structure orientation enclosing nearly all the water initially present. A dispersed system of these crystallites is referred to as a "sol". The stability of this system is believed to be, in part, a result of the presence of a surface charge on the crystallites which serves to keep them apart. Moreover, the stability of this system is also believed to be due, in part, to the low solubility of the crystallites in the aqueous solution. The open structure which results from the transformation of the crystallites is referred to as a "gel". The porosity of a typical sol-gel matrix may be as high as 90%. The transition from sol to gel is necessarily slow (relative to conventional precipitation procedures) to ensure that a matrix having homogeneous texture is obtained. Accordingly, in general terms, a sol-gel process, may be considered as the dispersion of solid starting materials into their elementary units and the subsequent reconstruction of these units in a controlled and specifically oriented manner.

The biomass suitable for use in the present invention is not particularly restricted and may be any microorganism which is capable of adsorbing heavy metal. Examples of such microorganisms include, but are not limited to, algae, fungus, yeasts and the like. Specific examples of biomass which are suitable for use include *Penicillium sp, Steptomyces levoris, Chlorella vulgaris, Saccharomyces cerevisiae, Rhizopua arrhizus, R. oligosporous* and mixed culture sewage sludges. The most preferred biomass is *Pencillium sp*.

The initial step in the production of the bioadsorption composition of the present invention comprises reacting the biomass, a matrix compound and a metal compound to obtain a sol in dispersion. The matrix compound is selected from the group comprising silicates, aluminates and compounds comprising magnesium ion. The preferred matrix compound is a silicate, more preferably a metal silicate. Examples of suitable metal silicates include $C_1$-$C_6$ tetraalkyl-ortho-silicates, alkali or alkaline earth silicates and $C_1$-$C_6$ tetraalkoxy silanes. The preferred matrix compound suitable for use is selected from one of sodium silicate and tetraethyl-ortho-silicate. The most preferred matrix compound suitable for use is sodium silicate. The choice of metal compound suitable for use in the initial step of process is not particularly restricted. Preferably the metal compound is a metal halide, a metal acetate or a metal alkoxide. Examples of suitable metal halides include magnesium chloride, aluminum chloride, tin chloride and barium chloride. Examples of suitable metal acetates include titanium acetate, zirconium acetate and barium acetate. Examples of suitable metal alkoxides include aluminum tri(sec-butoxide), $C_1$-$C_6$ titanium alkoxides, $C_1$-$C_6$ zirconium alkoxides and $C_1$-$C_6$ tin alkoxides. The most preferred metal compound is aluminum chloride.

The order of addition of the reactants for step (i) of the process (i.e. sol formation) for producing the bioadsorption composition is not particularly restricted. In one embodiment of step (i), the biomass is dispersed in an aqueous solution of the metal compound after which an aqueous solution of the matrix compound (e.g. metal silicate) is added to the dispersion. In another embodiment of step (i), the biomass is dispersed in an aqueous solution of the matrix compound (e.g. metal silicate) after which an aqueous solution of the metal compound is added to the dispersion.

Step (ii) of the process involves hydrolyzing the sol produced from step (i) to form thereby a dispersion of the sol-gel matrix. The specific mode of hydrolysis is not particularly restricted. In one embodiment, the sol is hydrolyzed by being contacted with a base, preferably an aqueous solution of ammonia. In another embodiment, the sol is hydrolyzed by being contacted with an acid, preferably acetic acid. In yet another embodiment, the sol is hydrolyzed by being contacted with an organic solvent, preferably selected from the group comprising alcohols, ketones and esters, more preferably an alcohol, most preferably ethanol.

Regardless of the mode of hydrolysis of the sol, the result is a dispersion of a biomass encapsulated sol-gel matrix. This sol-gel matrix may then be filtered and the filter residue thereof dried in accordance with techniques known to those skilled in the art.

A bioadsorption composition comprising the resultant biomass encapsulated sol-gel matrix is suitable for use in the removal of heavy metal from waste water effluents. The waste water effluent, which is typically in the form of a dilute aqueous solution, may be an industrial process effluent, a waste stream solution, mine water effluent and the like. Thus, the bioadsorption composition of the present invention may be used to remove from waste water effluents (i) base metals such as cadmium, zinc and copper; (ii) heavy metals such as mercury, lead and uranium; and/or (iii) precious metals such as gold, silver, platinum and palladium. Moreover, the bioadsorption composition of the present invention is stable enough to endure repeated loading and unloading of heavy metal.

In use, the bioadsorption composition of the present invention is contacted with a heavy metal bearing waste water effluent with the result that a substantial amount of heavy metal from the waste water effluent is adsorbed by the bioadsorption composition—i.e. the bioadsorption composition is "loaded" with heavy metal. In a preferred embodiment the "loaded" bioadsorption composition is thereafter "unloaded" by contacting it with an elution solution to eluate thereby a substantial amount of the heavy metal from the "loaded" bioadsorption composition. The dissolved heavy metal may be obtained from the elution solution using conventional precipitation and recovery (e.g. filtration) techniques known to those skilled in the art.

The choice of elution solution suitable for use to "unload" heavy metal from the bioadsorption composition is not particularly restricted. Examples of suitable eluants include solutions of ethylenediaminetetraacetic acid (EDTA), hydrochloric acid, sulphuric acid, alkali (e.g. potassium, sodium, etc.) halides, carbonates, citrates, tartrates and oxalates. The preferred eluant solutions are alkali chlorides, sulphuric acid and EDTA.

Preferably, the waste water effluent which is treated with the bioadsorption composition of the present invention has a pH of from about 3.5 to about 5.0. In some instances, this necessitates raising the pH of what would ordinarily be considered an acidic waste water effluent (e.g. pH 2). For example, maintaining the pH of a mine water effluent at from about 3.5 to about 5.0 results in a reduced concentration of iron in solution thereby reducing competition for sites on the bioadsorption composition between iron and uranium, the latter being the preferred material for recovery.

Embodiments of the present invention will now be described with reference to the Examples, which Examples are not intended limit the scope of the invention.

EXAMPLE 1

Preparation of the Bioadsorption Composition

Two types of bioadsorption compositions were prepared in accordance with the procedures discussed below. Both types of bioadsorption compositions were based on a *Penicillium sp* biomass which as obtained by conventional techniques. The bioadsorption compositions were prepared as follows:

TYPE I: 10 g of biomass were dispersed in 100 mL of an aqueous solution of aluminum chloride (2.5% w/v) by stirring for 5 minutes. Thereafter, 50 mL of an aqueous solution of sodium silicate (5% w/v) and 15 mL of an aqueous solution of ammonia (10% v/v) were added to the dispersion and stirring was continued for 1 minute. The resultant dispersion comprising the biomass encapsulated sol-gel matrix was filtered for 30 minutes and thereafter dried for 2 hours at 85° C. yielding approximately 11 g of the biomass encapsulated sol-gel matrix which was useful as a bioadsorption composition.

TYPE II: 10 g of biomass were dispersed in 100 mL of an aqueous solution of sodium silicate (2.5 g w/v) by stirring for 5 minutes. Thereafter, 50 mL of an aqueous solution of aluminum chloride (5% w/v) and 15 mL of ethanol were added to the dispersion and stirring was continued for 1 minute. The resultant dispersion comprising biomass encapsulated sol-gel matrix was filtered for 30 minutes and thereafter dried for 2 hours at 85° C. yielding approximately 12 g of the biomass encapsulated sol-gel matrix which was useful as a bioadsorption composition.

EXAMPLE 2

Loading an Elution of the Bioadsorption Composition

A number of loading-elution tests were conducted using 3 g samples of the bioadsorption composition Types I and II prepared in Example 1. The waste water effluent used throughout this Example was uranium bearing mine water. The mine water, as received, had a pH of 2 and a uranium concentration of 49 ppm. Prior to loading, the pH of the mine water was adjusted to 4.2 by addition of sodium hydroxide, which resulted in a decrease in uranium concentration to from 41.5 to 47 ppm. The elements used were aqueous solutions of sodium carbonate and sodium chloride.

The laboratory apparatus comprised a glass column having a diameter of 1.1 cm and an approximate height of 10 cm. Thus, the column hag a volume of approximately 10 mL of the sol-gel biomass ion exchange bed. The feedrate was controlled with a peristaltic pump and the column effluents were controlled by gravity.

For control purposes, an agitated batch loading test was conducted with 1 g of pure biomass in 1 L of mine water having a pH of 4. The loading time was 3 hours.

The throughput of the column during the loading-elution tests of this Example varied from 50 Bed Volume (hereinafter BV) to 200 BV during the loading stage, and from 8 BV to 50 BV during the elution stage. The basis for evaluating the results of the tests included the volumes and flowrates of the column effluents, in addition to their uranium and iron concentrations, and their pH values. The loading-elution capacities were derived from the actual weights of the bioencapsulated sol-gel matrices, the flowrates and uranium concentration differences between the mine water and the loading effluents, as well as from the volumes and uranium contents of the elution effluent.

The results of four loading-elution tests are provided in Tables 1 to 4 together with the respective test conditions.

TABLE 1

Bioadsorption composition: TYPE I
Flowrate: 0.7 L/hr
Eluant: $NaCl_{(aq)}$ (10% w/v)

| mode | time (min) | volume (ml) | effluents: U-conc. (ppm) | U-content (mg) | U-content (%) |
|---|---|---|---|---|---|
| loading | 0–30 | 359 | 18 | 8.8 | 57.6 |
|  | 30–60 | 365 | 39 | 1.3 | 8.2 |
|  | 60–90 | 375 | 42 | 0 | 0 |
|  | 90–120 | 360 | 43 | 0 | 0 |
|  | 120–150 | 365 | 42 | 0 | 0 |
|  | 150–165 | 172 | 43 | 0 | 0 |
| washing | 0–2 | 21 | 33 | 0.7 |  |
|  | 2–4 | 21 | 11 | 0.2 |  |
|  | 4–6 | 21 | 7.2 | 0.15 |  |
| eluting | 0–11 | 120 | 2.8 | 0.34 | 3.4 |
|  | 11–22 | 128 | 1.3 | 0.17 | 1.7 |
|  | 22–33 | 128 | 1.1 | 0.14 | 1.4 |
|  | 33–44 | 130 | 0.8 | 0.10 | 1.0 |
| washing | 0–2 | 21 | 1.4 | 0.03 |  |
|  | 2–4 | 21 | 4.0 | 0.08 |  |
|  | 4–6 | 21 | 8.6 | 0.18 |  |

TABLE 2

Bioadsorption composition: TYPE II
Flowrate: 0.7 L/hr
Eluant: $NaCl_{(aq)}$ (10% w/v)

| mode | time (min) | Volume (ml) | effluents: U-conc. (ppm) | U-content (mg) | U-content (%) |
|---|---|---|---|---|---|
| loading | 0–30 | 424 | 9.9 | 13.8 | 76.7 |
|  | 30–60 | 375 | 38 | 1.7 | 10.6 |
|  | 60–90 | 415 | 41 | 0 | 0 |
|  | 90–120 | 265 | 44 | 0 | 0 |
|  | 120–150 | 320 | 41 | 0 | 0 |
|  | 150–175 | 245 | 44 | 0 | 0 |
| washing | 0–2 | 20 | 37 | 0.74 |  |
|  | 2–4 | 21 | 15 | 0.32 |  |
|  | 4–6 | 21 | 11 | 0.23 |  |
| eluting | 0–11 | 128 | 4.1 | 0.52 | 3.4 |
|  | 11–22 | 130 | 1.8 | 0.23 | 1.5 |
|  | 22–33 | 126 | 1.0 | 0.13 | 0.8 |
|  | 33–45 | 120 | 0.9 | 0.11 | 0.7 |
| washing | 0–2 | 20 | 0.9 | 0.018 |  |
|  | 2–4 | 20 | 5.7 | 0.114 |  |
|  | 4–6 | 21 | 12.0 | 0.252 |  |

TABLE 3

Bioadsorption composition: TYPE I
Flowrate: 0.7 L/hr
Eluant: $Na_2CO_3{}_{(aq)}$ (10% w/v)

| mode | time (min) | Volume (ml) | effluents: U-conc. (ppm) | U-content (mg) | U-content (%) |
|---|---|---|---|---|---|
| loading | 0–30 | 394 | 21 | 7.1 | 46.2 |
|  | 30–60 | 395 | 34 | 2.0 | 12.8 |
|  | 60–90 | 314 | 43 | 0 | 0 |
|  | 90–120 | 288 | 35 | 0 | 0 |
|  | 120–150 | 295 | 35 | 0 | 0 |
|  | 150–181 | 330 | 43 | 0 | 0 |
| washing | 0–2 | 20 | 29 | 0.58 |  |
|  | 2–4 | 20 | 16 | 0.32 |  |
|  | 4–6 | 20 | 7.2 | 0.14 |  |
| eluting | 0–71 | 38 |  |  |  |
|  | 71–86 | 2 | 140 | 9.24 | 100 |
|  | 86–146 | 26 |  |  |  |

TABLE 4

| | | | effluents: | | U-content | |
|---|---|---|---|---|---|---|
| mode | time (min) | Volume (ml) | U-conc. (ppm) | | (mg) | (%) |

Bioadsorption composition: TYPE II
Flowrate: 0.7 L/hr
Eluant: Na$_2$CO$_3$ $_{(aq)}$ (10% w/v)

| mode | time (min) | Volume (ml) | U-conc. (ppm) | (mg) | (%) |
|---|---|---|---|---|---|
| loading | 0–30 | 392 | 24 | 7.2 | 43.2 |
| | 30–60 | 397 | 40 | 0.9 | 5.3 |
| | 60–90 | 380 | 40 | 0.9 | 5.3 |
| | 90–120 | 388 | 42 | 0.2 | 1.2 |
| | 120–150 | 398 | 43 | 0 | 0 |
| | 150–156 | 75 | 44 | 0 | 0 |
| washing | 0–2 | 20 | 39 | 0.78 | |
| | 2–4 | 21 | 13 | 0.27 | |
| | 4–6 | 21 | 10 | 0.21 | |
| eluting | 0–10 | 37 | 192 | 7.1 | 77.2 |
| | 10–795 | 71 | 30 | 2.1 | 22.8 |

The results shown in Tables 1 to 4 indicate that uranium may be loading on to the bioadsorption composition in amounts of 55.0% to 87.3% based on the amount of uranium initially contained in the mine water effluent.

By comparison, the results of the stirred batch loading test with pure biomass (which was conducted for control purposes) indicated that the uranium concentration remaining in the effluent solution was 39 ppm which leads to a loading capacity of from 5 to 10 mg uranium per gram of biomass.

Thus, the test results of this Example appear to indicate that in a number of cases, the bioadsorption composition of the present invention is useful for removing the same amount of uranium as the pure biomass.

EXAMPLE 3

Repeated Loading and Elution of the Bioadsorption Composition

In this Example, the bioadsorption composition of the present invention was subjected 10 loading-elution cycles using the uranium bearing mine water described in Example 2.

It has been found to be advantageous to pretreat the bioadsorption composition prior to its use in repeated loading-elution of heavy metal from waste water effluent. For this Example, the bioadsorption composition, referred to as Type III, was prepared according to the following procedure.

TYPE III: 7 g of Type II (see Example 1) bioadsorption composition was treated with 150 mL of an aqueous solution of sodium carbonate (10% w/v), then filtered and washed with 100 mL of distilled water. The remaining solids were washed with 100 mL of sulphuric acid (pH 3) and subsequently treated with 10 mL of an aqueous solution of sodium carbonate (10% w/v), followed by repeated washing with distilled water and ethanol. The bioadsorption composition was dried at 85° C. for 1 hour. The size fraction −0.3 mm (the portion passing through a screen size of 0.3 mm) was removed.

Using a glass column similar to the one described in Example 2, 3.05 g of Type III bioadsorption composition was subjected to the first of ten loading-elution cycles. It was found advantageous to remove the size fraction −0.425 mm of the bioadsorption composition after the first loading-elution cycle. Thus, the column load of bioadsorption composition for loading-elution cycles 2 to 10 was 2.17 g. A flowrate of approximately 40 BV/hr (i.e. 0.4 L/hr) was used for both loading and elution during each cycle. The eluant used for each cycle was an aqueous solution of sodium carbonate (5% w/v).

The results of the 10 cycle loading-elution test are provided in Table 5.

TABLE 5

Bioadsorption composition: TYPE III
Flowrate: 0.4 L/hr
Eluant: Na$_2$CO$_3$ $_{(aq)}$ (5% w/v)

| CYCLE | MODE | TIME (min) | VOLUME (mL) | EFFLUENT pH | [U] (ppm) | U (mg) | EXTRACTION (%) |
|---|---|---|---|---|---|---|---|
| 1 | loading | 0–14 | 106 | 7.4 | 0.2 | 4.4 | 99.5 |
| | | 14–28 | 104 | 5.4 | 0.7 | 4.2 | 98.3 |
| | | 28–42 | 100 | 4.8 | 10 | 3.2 | 75.9 |
| | | 42–56 | 101 | 4.6 | 24 | 1.8 | 42.2 |
| | | 56–68 | 90 | 4.5 | 28 | 1.2 | 32.5 |
| | washing | 0–6 | 59 | 4.4 | 16 | 0.94 | |
| | eluting | 0–7 | 32 | 10.6 | 400 | 12.8 | 86.5 |
| | | 7–14 | 34 | 11.4 | 35 | 1.2 | 8.1 |
| | | 21–29 | 49 | 11.8 | 0.6 | 0.03 | 0.2 |
| | washing | 0–6 | 58 | 12.0 | <0.1 | | |
| 2 | loading | 0–14 | 104 | 5.0 | <0.1 | 4.3 | 100 |
| | | 14–28 | 96 | 4.6 | 13 | 2.7 | 68.7 |
| | | 28–42 | 98 | 4.5 | 22 | 1.9 | 47.0 |
| | | 42–56 | 94 | 4.5 | 31 | 1.0 | 25.3 |
| | | 56–69 | 109 | 4.5 | 29 | 1.4 | 30.1 |
| | washing | 0–6 | 60 | 4.2 | | | |
| | eluting | 0–7 | 42 | 11.0 | 206 | 8.7 | 77.0 |
| | | 7–14 | 43 | 11.6 | 7.5 | 0.3 | 2.7 |
| | | 14–21 | 44 | 11.7 | <0.1 | | |
| | | 21–24 | 24 | 11.8 | <0.1 | | |
| | washing | 0–6 | 57 | 11.7 | | | |
| 3 | loading | 0–14 | 84 | 9.5 | <0.1 | 3.5 | 100 |
| | | 14–28 | 84 | 5.1 | 3.6 | 3.2 | 91.3 |
| | | 28–45 | 102 | 4.8 | 20 | 2.2 | 51.8 |
| | | 45–56 | 56 | 4.7 | 30 | 0.6 | 27.7 |
| | | 56–70 | 82 | 4.6 | 31 | 0.9 | 25.3 |
| | | 70–85 | 97 | 4.5 | 38 | 0.3 | 8.4 |
| | washing | 0–6 | 58 | 4.5 | | | |
| | eluting | 0–7 | 31 | 10.9 | 316 | 9.8 | 91.6 |
| | | 7–14 | 36 | 11.7 | 24 | 0.9 | 8.4 |

TABLE 5-continued

Bioadsorption composition: TYPE III
Flowrate: 0.4 L/hr
Eluant: Na$_2$CO$_3$ $_{(aq)}$ (5% w/v)

| CYCLE | MODE | TIME (min) | VOLUME (mL) | EFFLUENT pH | [U] (ppm) | U (mg) | EXTRACTION (%) |
|---|---|---|---|---|---|---|---|
| | | 14–21 | 36 | 11.9 | <0.1 | | |
| | | 21–28 | 43 | 11.9 | <0.1 | | |
| | washing | 0–6 | 56 | 11.9 | | | |
| 4 | loading | 0–27 | 166 | 5.7 | <0.1 | 6.9 | 100 |
| | | 27–52 | 146 | 4.6 | 20 | 3.1 | 51.8 |
| | | 52–78 | 136 | 4.5 | 33 | 1.2 | 20.5 |
| | | 78–104 | 142 | 4.5 | 36 | 0.8 | 13.3 |
| | | 104–129 | 158 | 4.5 | 33 | 1.3 | 20.5 |
| | washing | 0–6 | 60 | 4.5 | | | |
| | eluting | 0–7 | 38 | 10.7 | 241 | 9.2 | 69.2 |
| | | 7–14 | 47 | 11.4 | 13 | 0.6 | 4.5 |
| | | 14–21 | 38 | 11.5 | <0.1 | | |
| | | 21–24 | 28 | 11.5 | <0.1 | | |
| | washing | 0–6 | 56 | 11.7 | | | |
| 5 | loading | 0–87 | 500 | 4.5 | (38) | (1.8) | |
| | washing | 0–6 | 60 | 4.5 | | | |
| | eluting | 0–13 | 80 | 11.0 | 129 | 10.32 | |
| | washing | 0–6 | 58 | 11.6 | | | |
| 6 | loading | 0–79 | 500 | 4.6 | 25 | 8.3 | 39.8 |
| | washing | 0–6 | 60 | 4.5 | | | |
| | eluting | 0–11 | 80 | 11.0 | 98 | 7.8 | 100 |
| | washing | 0–6 | 58 | 11.6 | | | |
| 7 | loading | 0–29 | 204 | 5.0 | 5.6 | 7.3 | 86.5 |
| | | 29–58 | 204 | 4.5 | 38 | 0.7 | 8.4 |
| | | 58–72 | 89 | 4.4 | 45 | 0 | 0 |
| | washing | 0–6 | 58 | 6.6 | | | |
| | eluting | 0–5 | 22 | 10.6 | 377 | 8.3 | |
| | | 5–10 | 23 | 11.1 | 72 | 1.7 | 100 |
| | | 10–20 | 64 | 11.5 | 6.0 | 0.4 | |
| | washing | 0–6 | 56 | 11.7 | | | |
| 8 | loading | 0–72 | 500 | 4.54 | 20 | 10.8 | 51.8 |
| | washing | 0–6 | 54 | 4.48 | | | |
| | eluting | 0–16 | 80 | 11.02 | 130 | 10.4 | 96.3 |
| | washing | 0–6 | 58 | 11.64 | | | |
| 9 | loading | 0–69 | 500 | 4.7 | 22 | 9.75 | 47.0 |
| | washing | 0–6 | 60 | 4.5 | | | |
| | eluting | 0–49 | 75 | 11.0 | 120 | 9.0 | 92.3 |
| | washing | 0–6 | 20 | 11.4 | | | |
| 10 | loading | 0–43 | 259 | 5.0 | 20 | 5.6 | 51.8 |
| | | 43–78 | 240 | 4.5 | 38 | 0.8 | 8.4 |
| | washing | 0–6 | 60 | 4.5 | | | |
| | eluting | 0–7 | 40 | 11.0 | 141 | 5.6 | 87.5 |
| | | 7–12 | 41 | 11.5 | 5.8 | 0.2 | 3.1 |
| | washing | 0–6 | 56 | 11.5 | | | |

As illustrated in Table 5, the Type III bioadsorption composition is relatively stable with respect to repeated loading-elution. In this regard, the loading capacity of this bioadsorption composition appears to be similar to that of the pure biomass (see Example 2 for pure biomass).

We claim:

1. A bioadsorption composition suitable for removing heavy metal from waste water effluents, said bioadsorption composition being capable of repeated loading and unloading of heavy metal, and comprising a biomass encapsulated sol-gel matrix, said sol-gel matrix being prepared by a process comprising the steps of:
   (i) reacting a biomass selected from the group consisting essentially of *Pencillium sp., Streptomyces levoris, Chlorella vulgaris, Saccharomyces cerevisiae, Rhizopia arrhizus, R. oligosporous*, mixed culture sewage sludges, algae, fungus and yeast; a matrix compound selected from the group consisting of silicates and aluminates; and a metal compound selected from halides, acetates and alkoxides containing a metal selected from the group consisting of aluminum, tin, titanium and zirconium; to obtain a sol consisting essentially of a dispersion of crystallites of said biomass, said matrix compound and said metal compound;
   (ii) hydrolysing said sol to form thereby a dispersion of said sol-gel matrix; and
   (iii) filtering and drying the filter residue of said dispersion to obtain thereby said sol-gel matrix.

2. The composition defined in claim 1, wherein step (i) is conducted in an aqueous medium, said metal compound is a chloride containing a metal selected from the group consisting essentially of aluminum, tin, titanium and zirconium and said matrix compound is a metal silicate.

3. The composition defined in claim 2, wherein said metal chloride is aluminum chloride and said metal silicate is sodium silicate.

4. The composition defined in claim 1, wherein step (i) is conducted in an organic medium, said metal compound is an alkoxide containing a metal selected from the group consisting of aluminum, tin, titanium and zirconium, and said matrix compound is an organo-silicate compound.

5. The composition defined in claim 4, wherein said organo-silicate compound is tetraethyl-ortho-silicate and said metal alkoxide is aluminum tri(sec-butoxzide).

6. The composition defined in claim 1 or 5, wherein said biomass is *Penicillium sp.*

7. A process for producing a biomass encapsulated sol-gel matrix suitable for use in a bioadsorption composition, said process comprising the steps of:
(i) reacting a biomass selected from the group consisting essentially of *Penicillium sp., Streptomyces levoris, Chlorella vulgaris, Saccharomyces cerevisiae, Rhizopia arrhizus, R. oligosporous*, mixed culture sewage sludges, algae, fungus and yeast; a matrix compound selected from the group consisting of silicates and aluminates; and a metal compound selected from halides, acetates and alkoxides containing a metal selected from the group consisting of aluminum, tin, titanium and zirconium; to obtain a sol consisting essentially of a dispersion of crystallites of said biomass, said matrix compound and said metal compound;
(ii) hydrolysing said sol to form thereby a dispersion of said sol-gel matrix; and
(iii) filtering and drying the filter residue of said dispersion to obtain thereby said sol-gel matrix.

8. The process defined in claim 7, wherein said matrix compound is a metal silicate.

9. The process defined in claim 7, wherein step (i) is conducted in an aqueous medium, said metal compound is a chloride containing a metal selected from the group consisting of aluminum, tin, titanium and zirconium and said matrix compound is a metal silicate.

10. The process defined in claim 9, wherein said sol is prepared by dispersing said biomass in an aqueous solution of said metal compound and subsequently adding an aqueous solution of said metal silicate.

11. The process defined in claim 9, wherein said sol is prepared by dispersing said biomass in an aqueous solution of said metal silicate and subsequently adding an aqueous solution of said metal compound.

12. The process defined in claim 10, wherein step (ii) comprises hydrolyzing said sol by the addition of an aqueous solution of ammonia.

13. The process defined in claim 11, wherein step (ii) comprises hydrolyzing said sol by the addition of an organic solvent.

14. The process defined in claim 13, wherein said organic solvent is selected from the group consisting essentially of alcohols, ketones and esters.

15. The process defined in claim 13, wherein said organic solvent is an alcohol.

16. The process defined in claim 13, wherein said organic solvent is ethanol.

17. The process defined in claims, 9, 10, or 11, wherein said metal chloride is selected from the group consisting essentially of magnesium chloride, aluminum chloride, tin chloride and barium chloride.

18. The process defined in claim 9, wherein said metal compound is aluminum chloride.

19. The process defined in claim 9, wherein said biomass is *Pencillium sp.*

* * * * *